United States Patent [19]

Faxvog et al.

[11] 4,259,013

[45] Mar. 31, 1981

[54] OPTICAL METHOD FOR INSPECTING SPHERICAL PARTS

[75] Inventors: Frederick R. Faxvog; Robert W. Lewis, both of Rochester, Mich.

[73] Assignee: General Motors Corporation, Detroit, Mich.

[21] Appl. No.: 71,188

[22] Filed: Aug. 30, 1979

[51] Int. Cl.³ ............................................. G01N 21/89
[52] U.S. Cl. .................................................... 356/237
[58] Field of Search ................ 356/428, 445, 446, 235

[56] References Cited

U.S. PATENT DOCUMENTS 3,430,055  2/1969  Metzger ........................... 356/237 X
3,565,568  2/1971  Hock ..................................... 356/369

OTHER PUBLICATIONS

Haehner, "Inspection System for Round Objects", Western Elec. Tech. Dig. No. 6, pp. 29–30, 4/1967.

Primary Examiner—John K. Corbin
Assistant Examiner—Matthew W. Koren
Attorney, Agent, or Firm—Warren D. Hill

[57] ABSTRACT

Spherical parts such as ball bearings are inspected by rolling the parts down sizing rails so that they rotate rapidly with minimal translational motion at a point where they drop through the sizing rails. In a region of rapid rotation the part is inspected by an array of optical systems covering the entire area of the part. Each system focuses a small line of light on the part and in a direction slightly misaligned with the center of the part and the same optics focuses specularly reflected light from the part to a detection region where the light level is measured and a corresponding electrical signal is produced. When the line image scans over a defect, the resulting absorption or scattering of the light causes a rapid decrease in the light received at the measuring location so that a detectable change in the electrical signal occurs.

4 Claims, 5 Drawing Figures

OPTICAL METHOD FOR INSPECTING SPHERICAL PARTS

This invention relates to a method for inspecting spherical surfaces and more particularly to an optical method for such inspection.

It has been the previous practice to inspect the surface of a ball bearing while it is rolling down sizing rails by illuminating the ball by several light sources without the aid of focusing lenses and to attempt to detect each light image on the ball surface by detectors positioned around the ball. Changes in the detected light level indicated the presence of defects in the surface of the ball. In this manner large defects were detectable. Small ones, however, could not be found by this system. It has also been proposed to use an elaborate focusing and detecting optical system to form a single large round image on the surface of a spherical part and to detect variations in the light reflected therefrom. However, that arrangement also offers low sensitivity to small defects and the required elaborate optical hardware makes it impractical to simultaneously inspect several regions of the spherical part simultaneously due to space limitations.

It is, therefore, an object of this invention to provide a method of inspecting a surface of a spherical part which readily detects very small surface defects. It is a further object to provide such a method wherein simultaneous inspection of several adjacent surface areas of the part is feasible.

The invention is carried out by focusing along an optical axis a fine line of light onto the surface of the rotating vertical part by an optical system such that the optical axis is slightly misaligned with the center of the part and collecting light specularly reflected from the surface by the same optical system and focusing it to a measuring region such that light absorbed and scattered by a defect does not reach the measuring region thereby reducing the measured light intensity. The invention further comprehends electrically detecting the changes in light which represent the presence of a defect. The invention is further carried out by simultaneously focusing several lines of light on the spherical part by a plurality of line forming optics to inspect a large portion of or all of the part surface.

The above and other advantages will be made more apparent from the following specification taken in conjunction with the accompanying drawings wherein like reference numerals refer to like parts and wherein.

Figure 1:
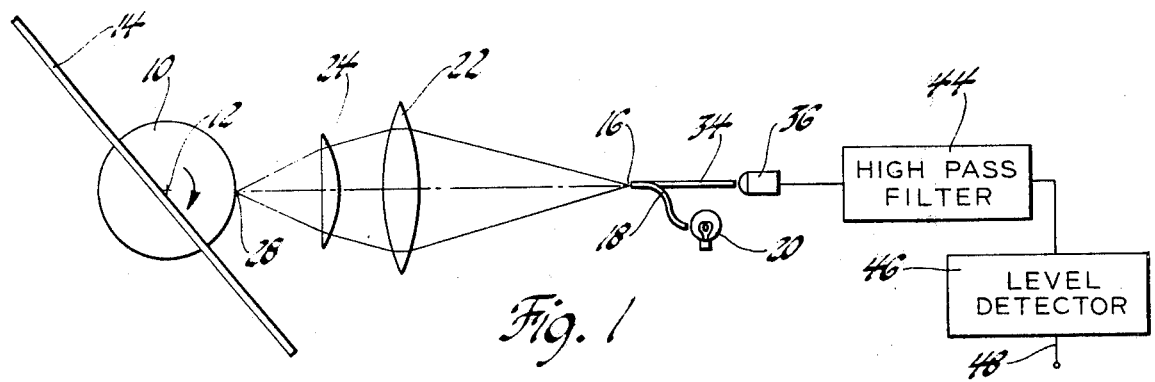
FIGS. 1 and 2 are side view and plan views respectively of an optical system in diagrammatic form embodying the method for inspecting a rotating spherical part according to the invention.
Figure 2:
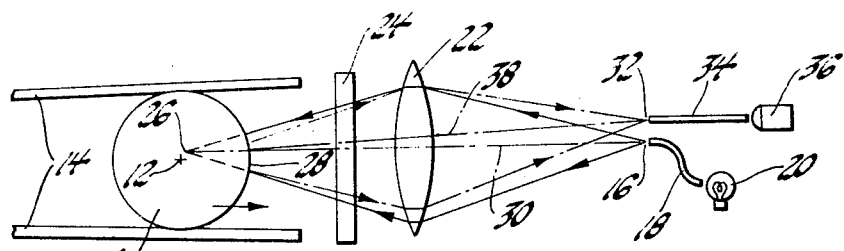

As shown in FIGS. 1 and 2 a spherical part such as a ball bearing 10 is caused to rotate about its center 12 by rolling down a pair of spaced sizing rails 14 which are inclined to cause the ball 10 to move along the rails. The rails 14 are divergent so that as the ball 10 approaches the point at which the rail spacing is nearly as great as the ball diameter, as shown in the figures, the rotational velocity of the ball becomes great with respect to its translational motion. It is at this point that it is desired to perform optical inspection for surface defects of the ball.

An optical inspection system includes a source of light 16 formed by a fiber optic element 18 of very small diameter illuminated by a lamp 20. A lens combination of a spherical lens 22 and a cylindrical (or toroidal) lens 24 focuses the light from the point 16 onto the surface of the ball 10 in a narrow real line image. As best shown in FIG. 2, the spherical lens 22 is so disposed relative to the light source and ball that it focuses the light toward a virtual line image which appears as a point 26 slightly spaced from the center 12 of the ball. Thus, the spherical converging wave front is nearly coincident with the spherical surface of the ball 10. As shown in FIG. 1, the cylindrical lens 24 is positioned to converge the light in one dimension to a narrow line image 28 on the ball 10 but not disturbing the light beam in the other dimension shown in FIG. 2.

The line defined by the source 16, the image 28 and the virtual focus point 26 defines the optical axis 30 of the illuminating light beam. If the optical axis 30 were aligned with the center 12 of the ball, the specularly reflected light from the ball surface would be focused by the lenses back to the point source 16. To avoid that condition, the optical axis 30 is misaligned with the center 12 so that the specularly reflected light is focused by the lenses 24 and 22 to a locus 32 spaced from the point source 16. A detector comprising a fiber optic conductor 34 and a photodetector 36 measure the light returned to the locus 32. The reflected light defines a second optical axis 38 slightly inclined to the first axis 30. Because the reflected light does not follow the same path as the incident light some of it will not enter the entrance pupil of the lens system. Moreover, as the ball 10 moves translationally along the rails 14 toward the inspection station, it gradually moves into the focus of the system and then out of focus so that the optical coupling is at first inefficient, gradually builds up to a peak, and then falls off. The inefficient coupling is due to the reflected light not being collected by the entrance pupil of the lens system and not being accurately focused at the detection locus 32 when the ball is displaced from the optimum position. Nevertheless, useful inspection is possible even when the reflected light is not collected most efficiently so that the inspection can occur over a range of ball positions allowing the ball to rotate several times while it is in the inspection range.

Figure 3:
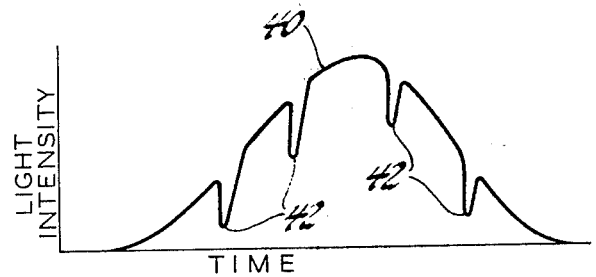
FIG. 3 is a graph indicating the variation in measured light reflected from the surface of the spherical part as it varies with respect to time.

FIG. 3 shows a representative graph of measured light intensity at locus 32 versus time. The general envelope of the light intensity 40 reveals the increase and decrease of measured light which occurs during ball movement to the inspection zone. A perfect ball would yield a smooth curve 40 without the dips 42. Whenever a defect traverses through the line image 28, the light incident upon that defect is absorbed and/or scattered. The absorbed light, of course, does not reach the detection locus 32 and the scattered light will be spread over such a large angle that most of it also will not pass through the lens system to the point 32. Even that scattered light which passes through the optics will in the main be distributed in a diffraction pattern over a region surrounding the detection locus 32 so that very little of it is sensed by the photodetector 36. The net result is that when such a defect occurs, the measured light intensity is sharply reduced by an amount depending upon the nature and size of the defect. Such a defect accounts for the reduced intensity regions 42 in the curve of FIG. 3. Since the ball rotates several times as it passes through the inspection station, it will be understood that a single defect is scanned several times and several intensity reductions 42 occur.

As an example of an optical system suitable to inspect a ball 10 having a diameter of 10.32 mm, the fiber optic source is 0.5 mm diameter and emits about 5 microwatts of light power, the spherical lens has a focal length of 12 mm and a diameter of 13 mm, and the cylindrical lens has a focal length of 12.7 mm and is 5.25 mm square. The left surface of the spherical lens, as viewed in FIG. 1, is spaced 50 mm from the source 16, the left or flat side of the cylindrical lens 24 is 9 mm from the left side of the lens 22, and the flat side of the cylindrical lens is 3.35 mm from the nearest point on the ball 10. The resulting size of the image is approximately 0.1 mm by 2 mm. Due to the narrowness of the image, this arrangement is very sensitive to defects and will detect 0.25 mm diameter pits in the surface.

A variation of the optical system of FIG. 1 involves arranging the lenses so that the optical axis is aligned with the center of the ball but the light is focused to a virtual line image at a position slightly in front of or behind the center of the ball. Then the spot reflected back to the detection region is defocused to cover an elongated area much larger than the source but generally centered on the source. This allows a very small diameter optical fiber (or several spaced fibers) to be used as the source and placed directly in front of a photodetector. Since the return spot is relatively large, the source fiber will shade only a small portion of it.

Referring again to FIG. 1, an electronic detection system is useful in analyzing the electrical signal generated by the photodetector 36, which signal is proportional to the light intensity curve as represented in FIG. 3. A high pass filter 44 is connected to the output of the photodetector 36 and a level detector 46, in turn, is connected to the output of the filter 44 which is tuned according to the scan rate over the surface. The purpose of the high pass filter is to pass only the high frequency signals associated with the reduced intensity portions 42 of the measured signal and to suppress the slowing changing value 40 representing the changing efficiency of the optical coupling. The level detector 46 will be set to produce an output on line 48 whenever a signal reduction 42 has a sufficient rate of change to represent a surface defect in the ball 10.

Figure 4:
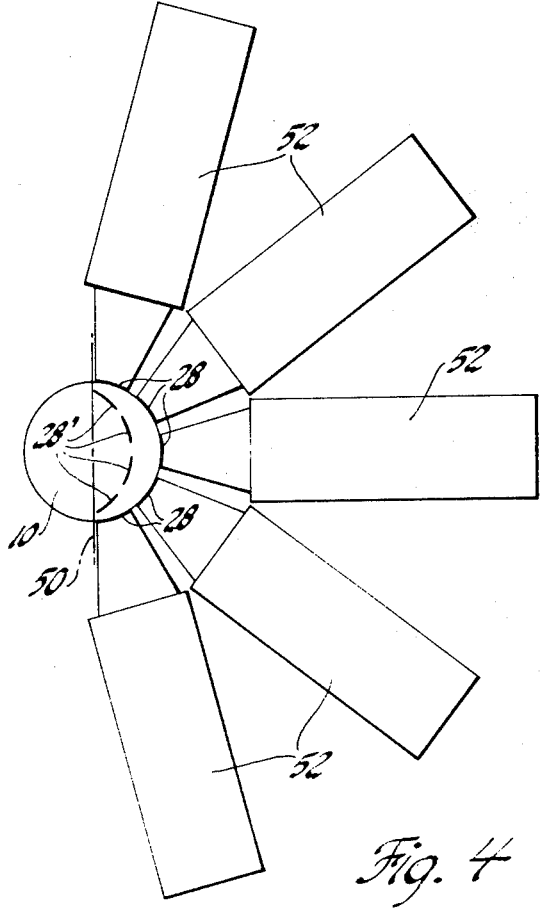
FIG. 4 is a diagrammatic view of an inspection system operating according to the method of the invention and employing a plurality of simultaneously operating inspection units.
Figure 5:
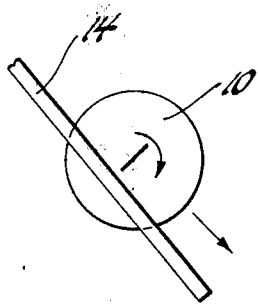
FIG. 5 is a view of a spherical part illuminated at the area around its axis of rotation.

The line 28 sweeps a path over the surface of the rotating ball to effect inspection of the path. As shown in FIG. 4, inspection of the total ball surface is accomplished by arranging an array of optical inspection units 52 about a ball 10 rotating on an axis 50. Each unit is like the system of FIGS. 1 and 2. Due to the space requirements of the optical units, a single tier of the units 52 may not provide full coverage; that is, there will be spaces between the fine line images 28 projected onto the ball 10. A second tier of optical units, not shown in the drawings for purposes of clarity, project a second array of four line images 28' positioned to sweep through paths overlapping the paths scanned by the images 28 to provide complete inspection of the ball surface except the end surfaces which are in contact with or near the rails 14. Additional optical units placed further up the rails 14 where the ball rides higher in the rails inspect the end portions of the ball as shown in FIG. 5. Since the ball is rotating more slowly at that point, different electronic filters would be used to accommodate the slower scan rate.

It will thus be seen that according to this invention there is provided a method of inspecting the surface of a rotating ball by forming a line image on the ball by an optical assembly and projecting light specularly reflected from a ball to a measuring locus using the same optics and to detect the presence of flaws by the rate of change of the measured light at the measuring locus, and further to simultaneously inspect multiple areas of the ball in order to provide complete surface coverage.

The embodiments of the invention in which an exclusive property or privilege is claimed are defined as follows:

1. The method of optically inspecting the surface of a spherical part comprising the steps of
    rotating the spherical part about its center,
    directing light in a focused form from light forming optics onto the surface of the part in a narrow real line image such that the light is focused toward a virtual line image slightly spaced from the center of the part,
    focusing by the said optics light reflected from the said real line image to a detection region, and
    measuring the focused reflected light comprising chiefly that reflected from a perfect part surface at a specific locus in the said region such that most of the light scattered or absorbed by a surface defect does not reach the locus thus reducing the measured light when a defect is illuminated by the line image.

2. The method of optically inspecting the surface of a spherical part comprising the steps of
    rotating the spherical part about its center,
    directing light in a focused form from light forming optics onto the surface of the part in a narrow line image such that the optical axis of the resulting light path is slightly misaligned with the center of the part,
    focusing by the said optics light reflected from the said line image along a second optical axis inclined to the first said optical axis to a detection region, and
    measuring the focused reflected light comprising chiefly that reflected from a perfect part surface at a specific locus in the said region such that most of the light scattered or absorbed by a surface defect does not reach the locus thus reducing the measured light when a defect is illuminated by the line image.

3. The method of optically inspecting the surface of a spherical part comprising the steps of
    rotating the spherical part about an axis passing through its center by supporting the part at spaced locations near its axis and rolling the part through an inspection zone,
    directing light in a focused form from light forming optics onto the surface of the part in a narrow line image such that the optical axis of the resulting light path is slightly laterally spaced from the center of the part,
    focusing by the said optics light reflected from the said line image along a second optical axis inclined to the first said optical axis to a detection region,
    measuring the focused reflected light comprising chiefly that reflected from a perfect part surface at a specific locus in the said region such that most of the light scattered or absorbed by a surface defect does not reach the locus thus sharply reducing the measured light when a defect is illuminated by the line image, and producing an electrical signal corresponding to the measured light level, and electronically detecting signal changes representing defects.

4. The method of optically inspecting the surface of a spherical part comprising the steps of rotating the spherical part about its center, directing light in a focused form from a plurality of light forming optics onto the surface of the part in a plurality of spaced overlapping narrow line images such that the respective optical axis of each resulting light path is slightly misaligned with the center of the part and each line image sweeps over a path on the surface, focusing each of the said optics light reflected from its respective line image along a respective second optical axis inclined to the respective first said optical axis to a detection region, and measuring the focused reflected light comprising chiefly that reflected from a perfect part surface at a specific locus in each of the said regions such that most of the light scattered or absorbed by a surface defect does not reach the respective locus thus reducing the measured light when a defect is illuminated by the line image, whereby the part is inspected over a surface area comprising the composite paths swept by all the said line images.

* * * * *